(12) United States Patent
Omura et al.

(10) Patent No.: US 7,439,225 B2
(45) Date of Patent: Oct. 21, 2008

(54) SUBSTANCES K01-B0171 AND PROCESS FOR PRODUCING THE SAME

(75) Inventors: Satoshi Omura, Tokyo (JP); Hiroshi Tomoda, Tokyo (JP); Masato Iwatsuki, Tokyo (JP); Yoko Takahashi, Tokyo (JP)

(73) Assignee: The Kitasato Institute, Tokyo (JP)

( * ) Notice: Subject to any disclaimer, the term of this patent is extended or adjusted under 35 U.S.C. 154(b) by 406 days.

(21) Appl. No.: 10/508,413

(22) PCT Filed: Jan. 17, 2003

(86) PCT No.: PCT/JP03/00349

§ 371 (c)(1),
(2), (4) Date: Jun. 14, 2005

(87) PCT Pub. No.: WO2004/065413

PCT Pub. Date: Aug. 5, 2004

(65) Prior Publication Data

US 2006/0089298 A1    Apr. 27, 2006

(51) Int. Cl.
*A61K 38/12* (2006.01)
(52) U.S. Cl. .......................................... 514/9; 530/315
(58) Field of Classification Search ....................... None
See application file for complete search history.

(56) References Cited

U.S. PATENT DOCUMENTS 4,374,764 A    2/1983  Arai et al.

OTHER PUBLICATIONS

Hart et al., Australian and New Zealand Journal of Medicine, 1988, vol. 18, No. 6, pp. 790-791.*
Miyakawa, Y. et al., "In vitro activity of the antimicrobial peptides human and rabbit defensins and porcine leukocyte protegrin against Mycobacterium tuberculosis", Infection and Immunity, (1996), vol. 64, No. 3, pp. 926 to 932, abstract.
Hart, D.H. et al., "Lung infection caused by *Rhodococcus*", Australian and New Zealand Journal of Medicine, (Oct. 1988), vol. 18, No. 6, pp. 790 to 791, abstract.
A. Maureen Rouhi, Chemical and Engineering News, May 17, pp. 52-69, 1999.
N. Saitou et al., "The Neighbor-joining Method: A New Method for Reconstructing Phylogenetic Trees", Mol. Biol. Evol. 4: 406-425, 1987.

* cited by examiner

*Primary Examiner*—Christopher R. Tate
*Assistant Examiner*—Roy Teller
(74) *Attorney, Agent, or Firm*—Young & Thompson

(57) ABSTRACT

The present invention is comprised of culturing a microorganism having ability to produce K01-B0171-B substance and/or K01-B0171-C substance in a medium, accumulating K01-B0171-B substance and/or K01-B0171-C substance in a culture fluid and isolating K01-B0171-B substance and/or, K01-B0171-C substance from the culture fluid. The obtained K01-B0171-B substance, K01-B0171-C substance or a composition of these substances is expected to be useful as a medicament of antituberculous agent.

9 Claims, 8 Drawing Sheets

SUBSTANCES K01-B0171 AND PROCESS FOR PRODUCING THE SAME

TECHNICAL FIELD

The present invention relates to novel K01-B0171 substance having antituberculous activity and production thereof. More particularly, the present invention relates to K01-B0171 substance, which is a useful substance for prevention and treatment of tuberculosis, as an antituberculous agent consisting of K01-B0171-B substance and K01-B0171-C substance.

BACKGROUND ART

About one-third of human beings in the world is estimated to be infected with tubercle bacillus, and three million peoples are reported to die of tuberculosis. Tuberculosis is an important problem for jeopardizing human beings in under-developed countries and recently in advanced countries as a causative bacterium for the mass infection in schools, medical institutions and facilities for the aged as well as in the opportunistic infection in patients with AIDS. At present, although isoniazid, rifampicin, kanamycin and ethambutol are used as antituberculous agents, novel antituberculous agents having different chemical structure or mechanism of action are demanded due to occurring problems on resistant bacteria and side effects such as allergy, nephropathy and hepatopathy (A. Maureen Rouhi, Chemical and Engineering News, May 17, pp. 52-69, 1999).

DISCLOSURE OF THE INVENTION

Under such circumstance, discovering novel substance as the antituberculous agent having mechanism of action for solving problems such as allergy, nephropathy and hepatopathy is expected to contribute as a novel medicament for human welfare.

An object of the present invention is to provide novel K01-B0171 substance satisfying such expectation and having antituberculous activity effective for tubercle bacillus and process for production thereof.

We have extensively studied on metabolites produced by microorganisms in order to solve such problems and have found that substance having antituberculous activity was produced in culture fluid of a newly isolated microbial strain K01-B0171. Further, we have found substance having chemical structures represented by the formula [I] and [II] as a result of isolating and purifying active principle showing antituberculous activity from the culture fluid. Since the substances having such chemical structures have not been known before, each substance was designated as K01-B0171-B substance and K01-B0171-C substance, and both substances are totally designated as K01-B0171 substance.

The present invention was completed according to such knowledge.

An object of the present invention is to provide K01-B0171-B substance represented by the chemical formula [I]:

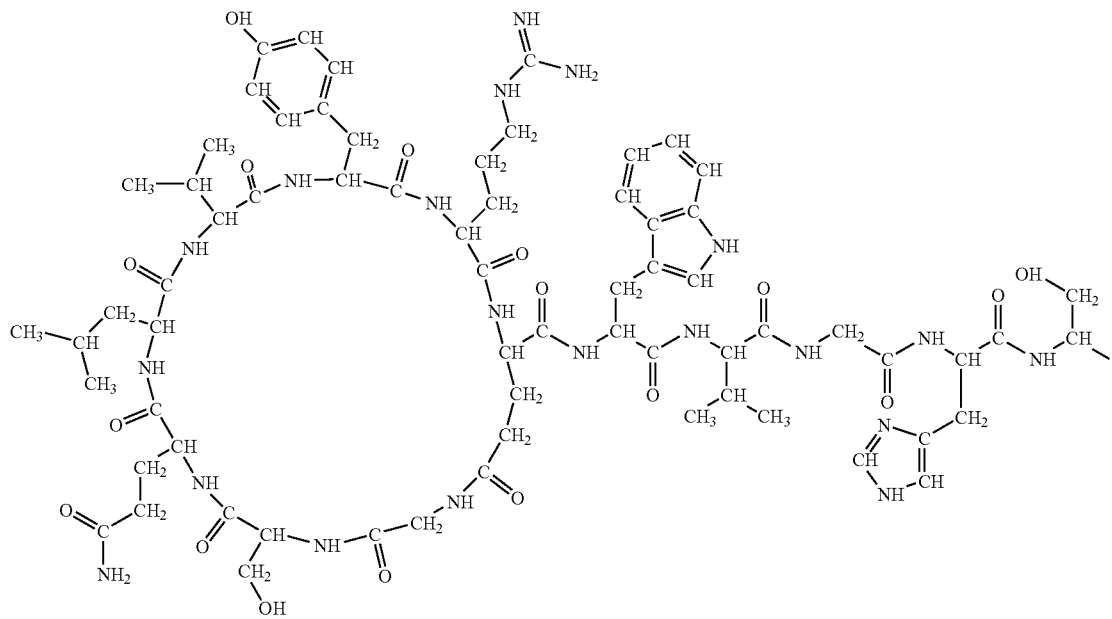

[I]

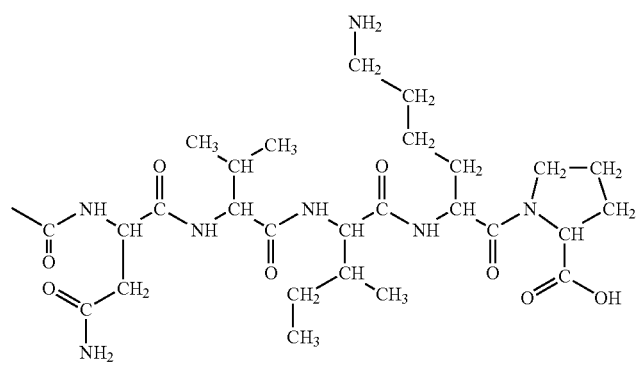

Another object of the present invention is to provide K01-B0171-C substance represented by the chemical formula [II]:
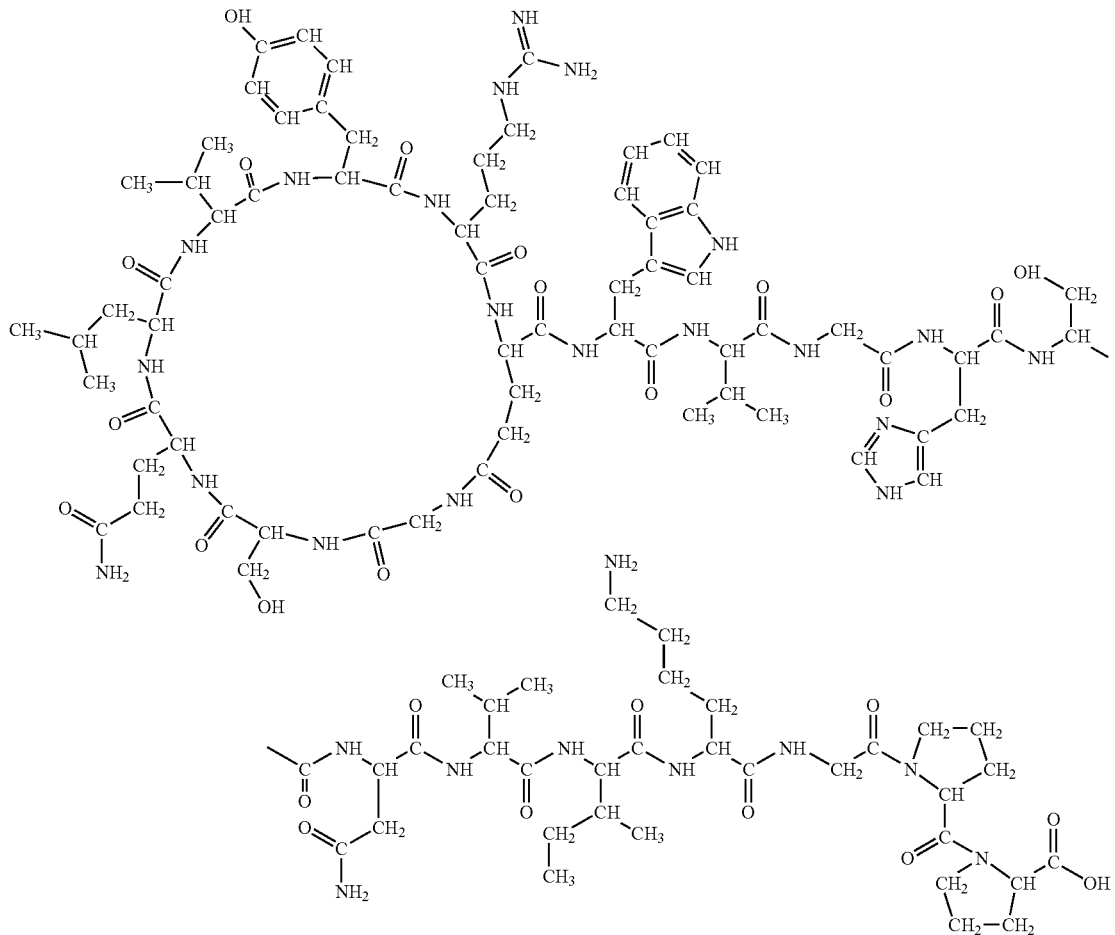
Further object of the present invention is to provide a composition of K01-B0171 substance comprising specifically K01-B0171-B substance represented by the chemical formula [I]:
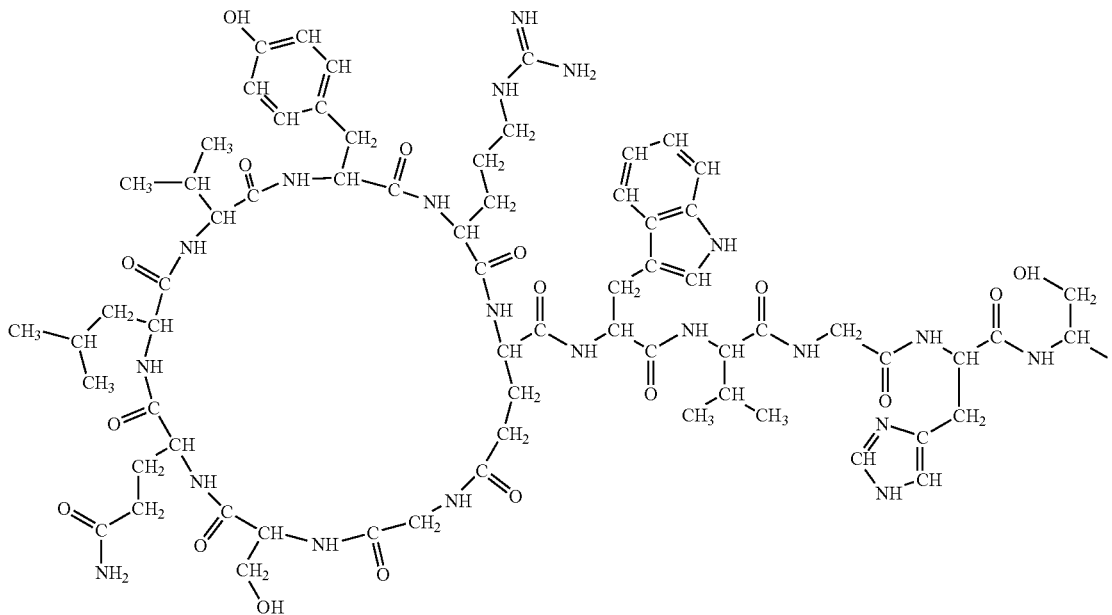

-continued

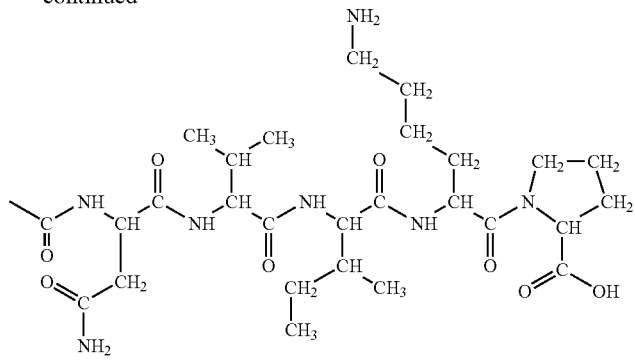

and specifically K01-B0171-C substance represented by the chemical formula [II]:

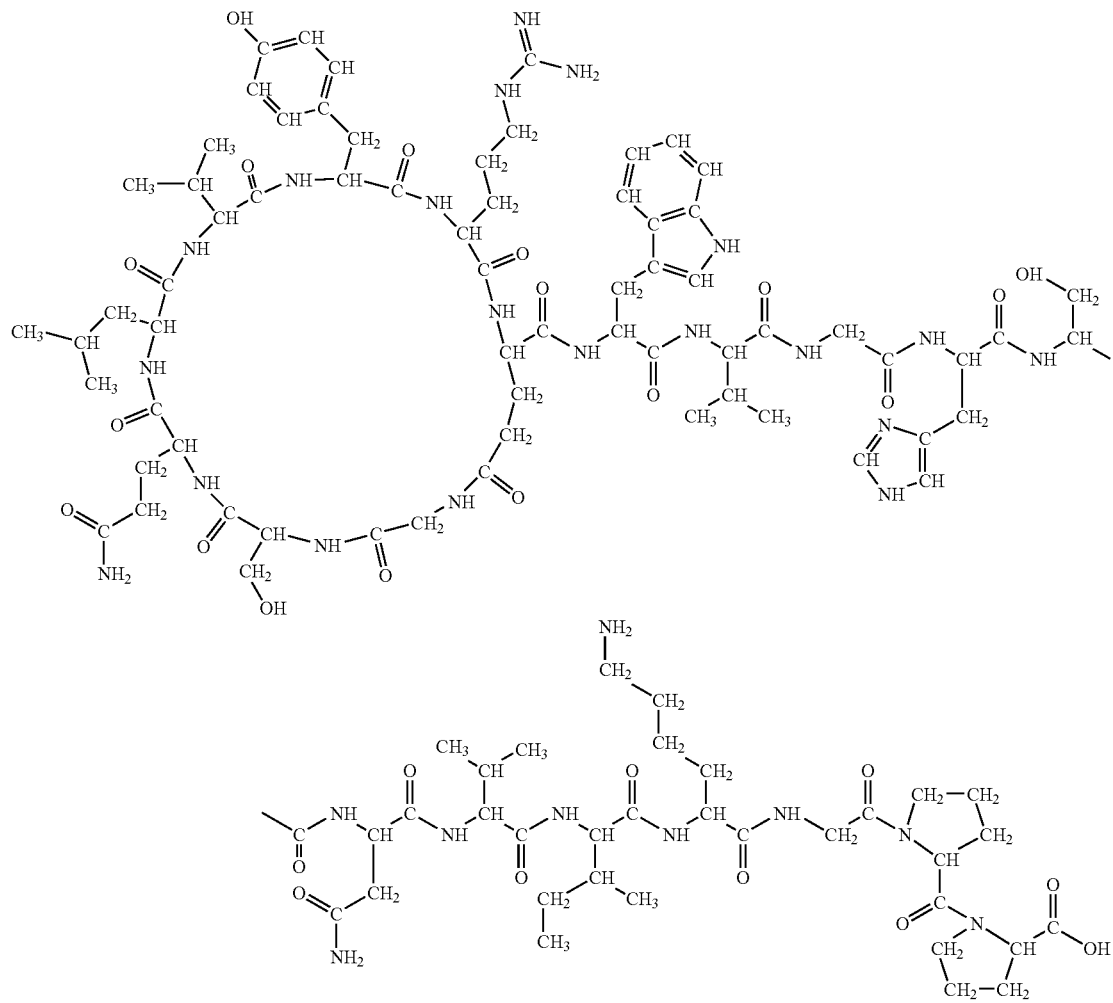

[II]

Further object of the present invention is to provide a process for production of K01-B0171-B substance comprising culturing a microorganism belonging to genus Rhodococcus and having ability to produce K01-B0171-B substance, accumulating K01-B0171-B substance in a culture fluid and isolating K01-B0171-B substance from the culture fluid.

Further object of the present invention is to provide a process for production of K01-B0171-C substance comprising culturing a microorganism belonging to genus *Rhodococcus* and having ability to produce K01-B0171-C substance, accumulating K01-B0171-C substance in a culture fluid and isolating K01-B0171-C substance from the culture fluid.

Further object of the present invention is to provide a process for production of a composition of K01-B0171 substance comprising culturing a microorganism belonging to genus *Rhodococcus* and having ability to produce K01-B0171-B substance and/or K01-B0171-C substance, accumulating K01-B0171-B substance and/or K01-B0171-C substance in a culture fluid and isolating K01-B0171-B substance and/or K01-B0171-C substance from the culture fluid.

Further object of the present invention is to provide a process for production of K01-B0171-B substance wherein a microorganism belonging to genus *Rhodococcus* and having ability to produce K01-B0171-B substance is *Rhodococcus* sp. K01-B0171 FERM BP-8267.

Further object of the present invention is to provide a process for production of K01-B0171-C substance wherein a microorganism belonging to genus *Rhodococcus* and having ability to produce K01-B0171-C substance is *Rhodococcus* sp. K01-B0171 FERM BP-8267.

Further object of the present invention is to provide a process for production of K01-B0171 substance consisting of K01-B0171-B substance and/or K01-B0171-C substance wherein a microorganism belonging to genus *Rhodococcus* and having ability to produce K01-B0171-B substance and/or K01-B0171-C substance is *Rhodococcus* sp. K01-B0171 FERM BP-8267.

Further object of the present invention is to provide a microorganism of *Rhodococcus* sp. K01-B0171 FERM BP-8276.

Further object of the present invention is to provide a composition consisting of K01-B0171-B substance, K01-B0171-C substance, or K01-B0171-B substance and K01-B0171-C substance used as an antituberculous agent.

The microorganism having ability to produce K01-B0171-B substance and K01-B0171-C substance or the composition consisting of these substances represented by the formula [I] and [II] (hereinafter designates as "K01-B0171 substance producing microorganism") belongs to genus *Rhodococcus*, and newly isolated strain *Rhodococcus* sp. K01-B0171 FERM BP-8267, deposited on *DATE DEPOSITED* at *NAME AND ADDRESS OF THE DEPOSITORY*, is an example, which can be used most effectively in the present invention.

Taxonomical properties of the strain *Rhodococcus* sp. K01-B0171 of the present invention are as follows.

(I) Morphological Properties

The strain shows good growth on Sucrose-nitrate agar medium, Glucose-asparagine agar medium, Glycerol-asparagine agar medium, Tyrosine agar medium, Oatmeal agar medium, Yeast-malt extract agar medium, Nutrient agar medium, Glucose-nitrate agar medium, Glycerol-calcium malate agar medium and Glucose-peptone agar medium. Medium growth was observed on Inorganic salts-starch agar medium and Peptone-yeast-iron agar medium. No epiphytic aerial mycelia were observed. On microscopic observation, cells are short bacilli to pseudococci, and the size is about 1.1-1.4 μm×0.7-0.8 μm.

(II) Culture Properties on Various Media

Culture properties of the producing strain of the present invention determined by the method of E. B. Shirling and D. Gottlieb (International Journal of Systematic Bacteriology, 16:313, 1966) are shown in the following Table. Color tone was determined referring to Color Harmony Manual, 4th Ed. (Container Corporation of America, Chicago, 1958) as a standard color, and color name and attached code number are indicated in the parenthesis. Unless otherwise noted, results are observation of cultures at 27° C. for 2 weeks on various media.

| Sucrose-nitrate agar medium | |
|---|---|
| Growth | good growth, light apricot (4ea) |
| Reverse side | fresh pink (4ca) |
| Soluble pigment | none |
| Glucose-asparagine agar medium | |
| Growth | good growth, fresh pink (4ca) |
| Reverse side | light melon yellow (3ea) |
| Soluble pigment | none |
| Glycerol-asparagine agar medium (ISP) | |
| Growth | good growth, biscuit (3ec) |
| Reverse side | light tan (3gc) |
| Soluble pigment | none |
| Inorganic salts-starch agar medium (ISP) | |
| Growth | moderate growth, pearl pink (3ca) |
| Reverse side | pearl pink (3ca) |
| Soluble pigment | none |
| Tyrosine agar medium (ISP) | |
| Growth | good growth, fresh pink (4ca) |
| Reverse side | fresh pink (4ca) |
| Soluble pigment | none |
| Oatmeal agar medium (ISP) | |
| Growth | good growth, light apricot (4ea) |
| Reverse side | light melon yellow (3ea) |
| Soluble pigment | none |
| Yeast-malt extract agar medium (ISP) | |
| Growth | good growth, light apricot (4ea) |
| Reverse side | light amber (3ic) |
| Soluble pigment | none |
| Nutrient agar medium | |
| Growth | good growth, fresh pink (4ca) |
| Reverse side | pearl pink (3ca) |
| Soluble pigment | none |
| Peptone-yeast-iron agar medium (ISP) | |
| Growth | moderate growth, biscuit (4ec) |
| Reverse side | honey gold (2ic) |
| Soluble pigment | slight growth, yellow |
| Glucose-nitrate agar medium | |
| Growth | good growth, fresh pink (4ca) |
| Reverse side | fresh pink (4ca) |
| Soluble pigment | none |
| Glycerol-calcium malate agar medium | |
| Growth | good growth, light apricot (4ea) |
| Reverse side | light apricot (4ea) |
| Soluble pigment | none |
| Glucose-peptone agar medium | |
| Growth | good growth, light apricot (4ea) |
| Reverse side | light melon yellow (3ea) |
| Soluble pigment | none |

(III) Physiological Properties

| (1) Formation of melanin pigment | |
|---|---|
| (a) Tyrosine agar | negative |
| (b) Peptone-yeast-iron agar medium | negative |
| (c) Tryptone-yeast liquid | negative |
| (d) Simple gelatin medium (21-23° C.) | negative |

-continued

| | |
|---|---|
| (2) Nitrate reduction | pseudopositive |
| (3) Liquefaction of gelatin (21-23° C.) (simple gelatin medium) | negative |
| (4) Starch hydrolysis | negative |
| (5) Coagulation of defatted milk (27° C.) | negative |
| (6) Peptonization of defatted milk (27° C.) | negative |
| (7) Growth temperature | 6-37° C. |
| (8) Utilization of carbon sources (Pridham-Gottlieb agar medium) | |
| Utilize: | D-glucose, D-mannitol, D-fructose, L-rhamnose, myo-inositol and sucrose |
| Not utilize: | L-arabinose, raffinose, melibiose and D-xylose, |
| (9) Decomposition of cellulose | negative |

(IV) Chemical Composition of Cell Wall 2,6-diaminopimelic acid of the cell wall is meso type. Total microbial sugar contains galactose and arabinose. The cell wall muramic acid is glycolyl type. Main menaquinone is MK-8 ($H_2$). Contains mycolic acid.

(V) Analysis of 16S rRNA Gene

Sequence of about 1300 bp (No. 131-No. 1350) in 16S rRNA gene is determined. As a result of molecular phylogenetic analysis according to neighbor-joining method (Saitou, N. and Nei, M. Mol. Biol. Evol. 4: 406-425, 1987) using data of strains belonging to genus Rhodococcus and other actinomycetes, which were registered and published in DNA Data Base, this strain can be systematized into genus Rhodococcus.

(VI) Conclusion

Taxonomical properties of the strain can be summarized as follows. Diaminopimelic acid of the cell wall is meso type. Total bacterial cell contains galactose and arabinose. The cell wall muramic acid is glycolyl type. Main menaquinone is MK-8 ($H_2$). Contains mycolic acid. Cells are short bacilli to pseudococci, and the size is about 1.1-1.4 μm×0.7-0.8 μm. Color tone of colonies shows orange color to brown. No melanin pigment is produced. On peptone-yeast-iron agar medium, yellow soluble pigment is slightly produced.

From these results and analysis of 16S rRNA gene, the strain is referred to genus Rhodococcus. The strain was deposited as Rhodococcus sp. K01-B0171 in International Patent Organism Depository, National Institute of Advanced Industrial Science and Technology, AIST Tsukuba Central 6, 1-1, Higashi 1-chome, Tsukuba-shi, Ibaraki-ken, 305-8566 Japan according to Budapest Treaty on the International Recognition of the Deposit of microorganism for the purpose of patent procedure on Jan. 6, 2003 as permanent depository number FERM BP-8267.

The strain of Rhodococcus sp. K01-B0171 can be mentioned as a preferable example of K01-B0171 substance producing strain used in the present invention. However, since the morphological properties of microorganisms are generally very easily mutated and are not constant. Natural mutation or artificial mutation generally performed by ultraviolet irradiation or chemical mutagens such as N-methyl-N'-nitro-N-nitrosoguanidine and ethyl methansulfonate, are well known. The strain belonging to genus Rhodococcus and having ability to produce K01-B0171 substance represented by the formula [I] and [II] hereinbefore, including the artificial mutants as well as natural mutants, can be used in the present invention.

In production of K01-B0171 substance of the present invention, at first, K01-B0171 substance producing strain belonging to genus Rhodococcus is cultured in a preferable medium. Nutrient sources preferable for production of K01-B0171 substance of the present invention are assimilable carbon sources for microorganism, digestible nitrogen sources and, if necessary, inorganic salts and vitamins. Examples of assimilable carbon sources are sugars such as glucose, fructose, maltose, lactose, galactose, dextrin and starch, and plant oil such as soybean oil, etc. are used independently or in combination.

Examples of nitrogen sources are peptone, yeast extract, meat extract, soybean powder, cotton seed powder, corn steep liquor, malt extract, casein, amino acids, urea, ammonium salts and nitrates are used independently or in combination. If necessary, salts such as phosphate, magnesium, calcium, sodium, potassium, heavy metallic salts such as iron, manganese, copper, cobalt or zinc, vitamins and substances suitable for production of K01-B0171 substance are added.

In the liquid culture, if foaming occurs, antifoam agents such as liquid paraffin, animal oil, vegetable oil, silicone oil and surface active agent can preferably be added. The above culture can be performed by liquid or solid culture condition, if the above nutrient sources are contained, and in general, the culture can preferably be performed using liquid culture medium, and in case of small production, the culture using flask is preferable.

In the large scale production using the large tank, in order to prevent delay of growth of microorganism in the production process, the production strain is inoculated and cultured initially in relatively small amount of culture medium, subsequently the cultured mass is transferred into the large tank and cultivation is preferably continued. In this case, compositions of the medium used in the pre-culture and the medium used in the production culture can be identical or different if necessary.

In the culture under aeration spinning condition, conventional means, for example, agitation using propeller and other mechanical stirring, rotation or shaking in fermenter, treating with pumping and blowing air can be applied. Air for aeration should be sterilized. Culturing temperature can be applied within ranges in the production of K01-B0171 substance by K01-B0171 substance producing strain, and the cultivation is performed usually at 6-37° C., preferably at 17° C. Culturing pH is usually pH 7-8, preferably about pH 7. Culturing time depends on culturing condition and is usually for 4 days.

The thus obtained accumulated K01-B0171 substance in the cultured mass exists generally in cultured mycelia. Isolation of K01-B0171 substance from the cultured mycelia can be performed by methods used for isolation of metabolites from microbial cultured mass independently, repeatedly or in combination with any orders of the means.

Isolation and collection of K01-B0171 substance can be performed by collecting from the mycelial extract. For example, the process can be performed by extracting the whole cultured mass with organic solvent such as acetone, ethanol or methanol. The extract is concentrated and is extracted with organic solvent such as chloroform and ethyl acetate. After concentration of the extract, the substance can be extracted with organic solvent such as chloroform and ethyl acetate. After concentration of the extract, K01-B0171 substance can be isolated by chromatography such as silica gel column chromatography, Sepahdex LH-20 column chromatography and ODS column chromatography.

Physicochemical properties of K01-B0171-B substance of the present invention are explained hereinbelow.

1. K01-B0171-B Substance
  (1) Nature: pale yellow powder
  (2) Melting point: 240° C. (decomp.)
  (3) Molecular formula: $C_{94}H_{143}N_{27}O_{25}$ HRFAB-MS(m/z) [M+H]Calculated 2051.0826, Found 2051.0764
  (4) Molecular weight: 2050 Observed by FAB-MS (m/z) as $[M+H]^+$ 2051

(5) Ultraviolet absorption spectrum (in 50% methanol): as shown in FIG. 1, specific absorption maximum λmax at 203 nm (ε=225,200), 220 nm (ε=83,200) and 282 nm (ε=11,900)
(6) Infrared absorption spectrum (KBr Tablet): as shown in FIG. 2, specific maximum absorption λmax at 1643 cm$^{-1}$
(7) Specific rotation: $[\alpha]_D^{26}$=−19.6° (c=0.5, 50%aqueous-methanol)
(8) Solubility in solvent: soluble in water, dimethyl sulfoxide (DMSO), methanol and ethanol, and insoluble in acetonitrile, ethyl acetate, chloroform and acetone
(9) Grouping for acidic, neutral and basic: Weak basic substance
(10) $^1$H-proton nuclear magnetic resonance spectrum (in deuterium oxide) measured by using Varian NMR 400 MHz: Shown in FIG. 3. Chemical shift of hydrogen (ppm) is shown in the following table. 0.64 (3H), 0.66 (3H), 0.68 (3H), 0.72 (3H), 0.74 (3H), 0.79 (3H), 0.81 (3H), 0.90 (3H), 0.93 (3H), 1.05 (3H), 1.15 (3H), 1.35 (1H), 1.35 (2H), 1.40 (1H), 1.42 (1H), 1.58 (1H), 1.60 (2H), 1.65 (1H), 1.66 (1H), 1.67 (2H), 1.72 (1H), 1.75 (2H), 1.76 (1H), 1.80 (2H), 1.84 (1H), 2.00 (1H), 2.03 (2H), 2.04 (1H), 2.10 (1H), 2.18 (1H), 2.30 (1H), 2.38 (2H), 2.60 (1H), 2.70 (1H), 2.83 (1H), 2.86 (1H), 2.98 (2H), 3.14 (1H), 3.16 (1H), 3.17 (2H), 3.30 (1H), 3.35 (1H), 3.62 (1H), 3.62 (1H), 3.70 (1H), 3.73 (1H), 3.74 (1H), 3.78 (1H), 3.80 (1H), 3.84 (1H), 3.92 (1H), 3.94 (1H), 4.10 (1H), 4.15 (1H), 4.28 (1H), 4.38 (1H), 4.43 (1H), 4.45 (1H), 4.47 (1H), 4.53 (1H), 4.69 (1H), 4.70 (1H), 4.73 (1H), 4.89 (1H), 4.94 (1H), 4.97 (1H), 5.15 (1H), 5.29 (1H), 6.70 (1H), 6.72 (2H), 7.00 (2H), 7.12 (1H), 7.22 (1H), 7.27 (1H), 7.48 (1H), 7.67 (1H), 8.60 (1H). ( ) indicates number of hydrogen atom.
(11) $^{13}$C-nuclear magnetic resonance spectrum (in deuterium oxide) measured by using Varian NMR 100 MHz: Shown in FIG. 4. Chemical shift of carbon (ppm) is shown in the following table. 13.20, 17.00, 20.10, 20.60, 20.80, 21.00, 21.30, 21.70, 23.70, 24.60, 24.70, 27.10, 27.40, 27.60, 27.80, 27.80, 28.60, 29.30, 29.70, 30.60, 31.80, 32.10, 32.60, 32.90, 34.00, 34.30, 34.40, 34.80, 38.30, 38.80, 40.10, 42.10, 43.40, 44.90, 45.30, 47.10, 50.60, 53.40, 53.70, 53.80, 54.80, 55.00, 56.20, 57.20, 57.40, 58.30, 58.60, 61.20, 61.30, 61.90, 62.00, 62.40, 63.70, 65.90, 68.80, 111.20, 114.90, 118.40, 119.30, 121.30, 122.30, 125.00, 127.70, 129.60, 131.40, 132.00, 133.60, 136.50, 139.30, 157.60, 159.70, 172.10, 174.20, 174.30, 174.76, 174.77, 174.80, 174.85, 174.90, 175.10, 175.20, 175.32, 175.33, 175.80, 175.93, 176.54, 176.75, 176.90, 177.00, 177.70, 178.80, 180.50.

As shown in above, as a result of detailed examination of various physico-chemical properties and spectral data of K01-B0171-B substance, K01-B0171-B substance was determined to have the chemical structure as shown in the following formula [I].

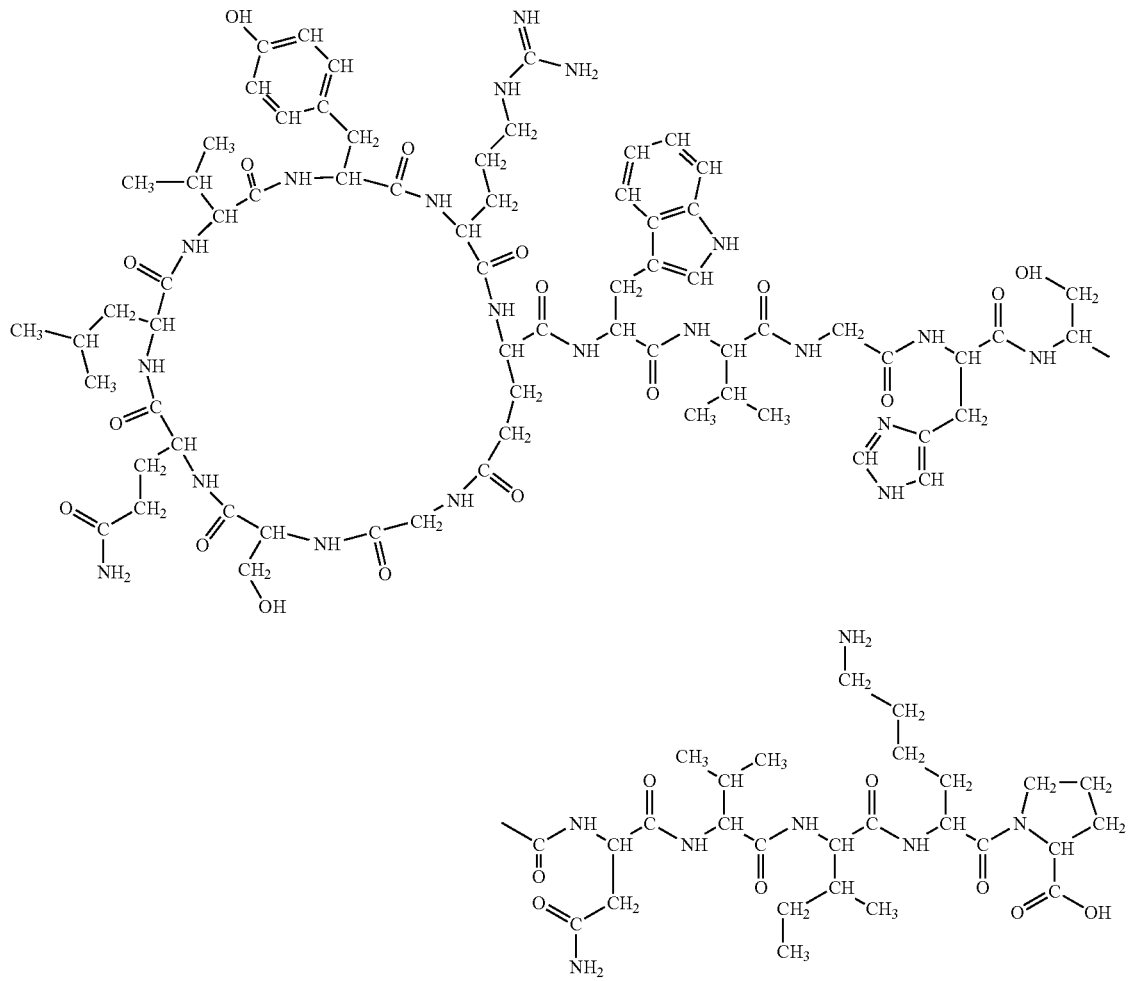

[I]

2. K01-B0171-C Substance
   (1) Nature: pale yellow powder
   (2) Melting point: 240° C. (decomp.)
   (3) Molecular formula: $C_{101}H_{153}N_{29}O_{27}$ HRFAB-MS(m/z)[M+H]$^+$ Calculated 2205.1568, Found 2205.1504
   (4) Molecular weight: 2204 Observed by FAB-MS (m/z) as [M+H]$^+$2205
   (5) Ultraviolet absorption spectrum (in 50% methanol): as shown in FIG. 5, specific absorption maximum λmax at 203 nm (ε=182,700), 220 nm (ε=66,800) and 284 nm (ε=9,800)
   (6) Infrared absorption spectrum (KBr Tablet): as shown in FIG. 6, specific maximum absorption λmax at 1650 cm$^{-1}$
   (7) Specific rotation: $[\alpha]_D^{26}$=−29.6° (c=0.5, 50% aqueous methanol)
   (8) Solubility in solvent: soluble in water, dimethyl sulfoxide (DMSO), methanol and ethanol, and insoluble in acetonitrile, ethyl acetate, chloroform and acetone
   (9) Grouping for acidic, neutral and basic: Weak basic substance
   (10) $^1$H-proton nuclear magnetic resonance spectrum (in deuterium oxide—deuteriomethanol (3:2)) measured by using Varian NMR 400 MHz: Shown in FIG. 7. Chemical shift of hydrogen (ppm) is shown in the following table. 0.59 (3H), 0.62 (3H), 0.70 (3H), 0.75 (3H), 0.76 (3H), 0.80 (3H), 0.82 (3H), 0.90 (3H), 0.94 (3H), 1.01 (1H), 1.15 (3H), 1.32 (1H), 1.33 (2H), 1.40 (1H), 1.43 (1H), 1.58 (1H), 1.60 (2H), 1.65 (1H), 1.66 (1H), 1.67 (2H), 1.74 (1H), 1.75 (2H), 1.76 (1H), 1.80 (2H), 1.80 (2H), 1.84 (1H), 1.99 (1H), 2.01 (1H), 2.02 (2H), 2.03 (2H), 2.04 (1H), 2.10 (1H), 2.18 (1H), 2.31 (1H), 2.32 (1H), 2.38 (2H), 2.48 (1H), 2.49 (1H), 2.84 (1H), 2.87 (1H), 2.99 (2H),.3.04 (1H), 3.08 (1H), 3.13 (2H), 3.31 (1H), 3.35 (1H), 3.48 (1H), 3.51 (1H), 3.54 (1H), 3.61 (1H), 3.68 (1H), 3.72 (1H), 3.76 (1H), 3.77 (1H), 3.78 (1H), 3.79 (1H), 3.81 (1H), 3.91 (1H), 3.94 (1H), 3.99 (1H), 4.07 (1H), 4.14 (1H), 4.21 (1H), 4.25 (1H), 4.43 (1H), 4.44 (1H), 4.49 (1H), 4.59 (1H), 4.64 (1H), 4.67 (1H), 4.92 (1H), 4.99 (1H), 5.14 (1H), 5.22 (1H), 5.25 (1H), 5.32 (1H), 6.35 (1H), 6.70 (2H), 6.99 (2H), 7.08 (1H), 7.18 (1H), 7.43 (1H), 7.55 (1H), 7.62 (1H), 8.42 (1H). ( ) indicates number of hydrogen atom.
   (11) $^{13}$C-nuclear magnetic resonance spectrum (in light water:deuteriomethanol (3:2)) measured by using Varian NMR 100 MHz: Shown in FIG. 8. Chemical shift of carbon (ppm) is shown in the following table. 11.13, 14.97, 17.89, 18.72, 18.85, 19.08, 19.32, 19.75, 21.65, 22.43, 22.49, 22.95, 23.10, 25.05, 25.13, 25.28, 25.73, 26.01, 26.67, 26.93, 27.46, 28.36, 30.29, 30.35, 31.05, 31.14, 31.89, 32.27, 32.44, 32.91, 36.07, 36.66, 38.08, 40.30, 41.08, 42.57, 43.30, 43.45, 45.29, 47.44, 48.05, 49.54, 51.40, 51.50, 51.74, 52.78, 54.23, 55.16, 55.93, 56.34, 58.95, 59.43, 59.99, 60.21, 61.35, 61.79, 62.81, 63.97, 67.20, 68.39, 109.21, 112.68, 116.35, 118.80, 119.05, 120.12, 122.72, 125.37, 127.57, 129.08, 131.60, 134.78, 136.15, 137.31, 155.70, 157.72, 168.61, 169.57, 171.07, 171.83, 172.15, 172.32, 172.40, 172.57, 172.83, 172.94, 172.99, 173.13, 173.67, 173.89, 174.02, 174.39, 174.71, 174.75, 174.80, 175.06, 178.56, 179.52, 180.15.

As shown in above, as a result of detailed examination of various physico-chemical properties and spectral data of K01-B0171-C substance, K01-B0171-C substance was determined to have the chemical structure as shown in the following formula [II].

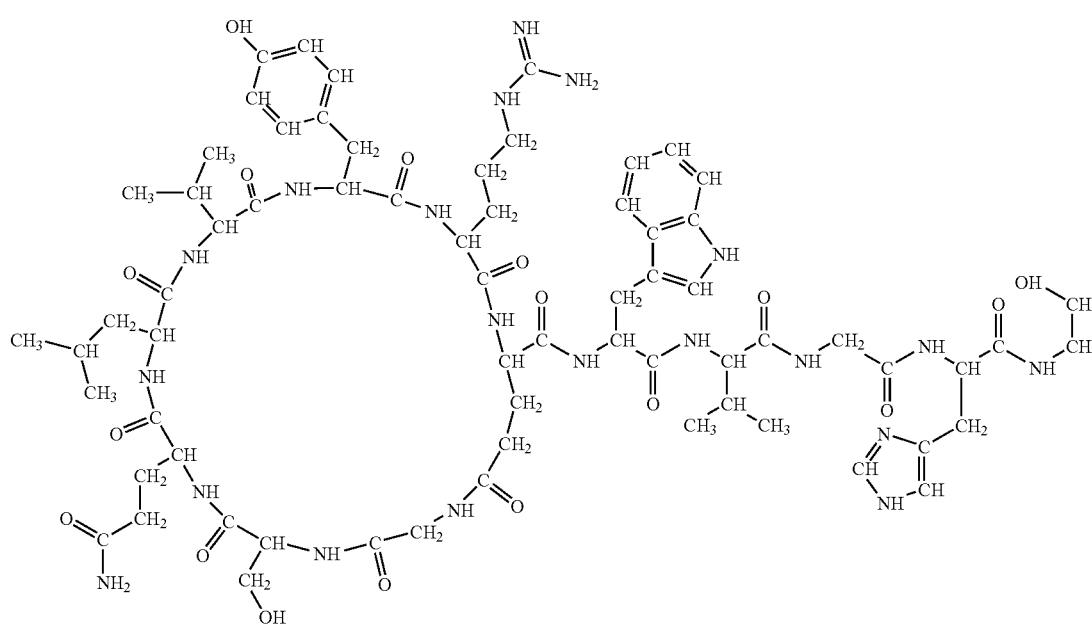

-continued

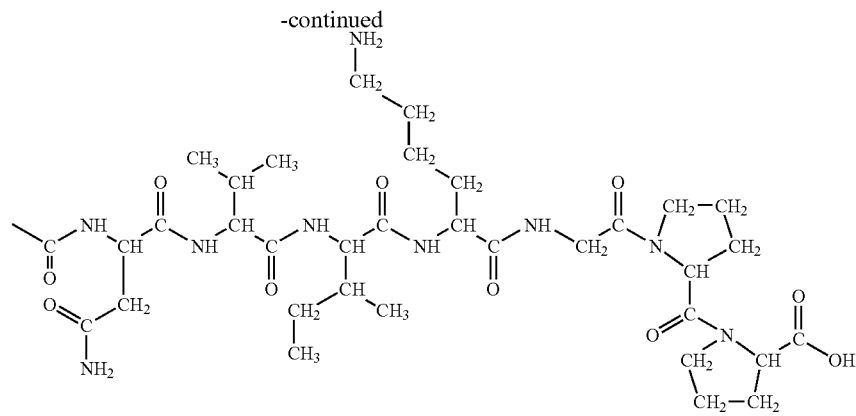

The biological properties of K01-B0171 substance of the present invention is described below. Antituberculous activity of K01-B0171 substance is measured by following two methods.

(1) Assay of Antituberculous Activity by Paper Disk Method

Mycobacterium smegmatis (Stock strain of Kitasato Institute for Life Sciences, Kitasato University) was inoculated at 0.3% in Waksman agar medium (peptone 0.5%, meat extract 0.5%, NaCl 0.5%, glucose 1.0% and agar 0.8%). Activity was evaluated by paper disk method (diameter 6 mm, ADVANTEC Inc., Japan) and inhibition zone was measured at 27° C. after culturing for 24 hours.

Result indicated that K01-B0171-B substance exhibited inhibition zone 19 mm in 10 μg/disk. K01-B0171-C substance exhibited inhibition zone 18 mm in 10 μg/disk.

(2) Assay of Antituberculous Activity by Liquid Culture Method

MIC was measured by modified broth microdilution method. One-loopful Mycobacterium smegmatis (Stock strain of Kitasato Institute for Life Sciences, Kitasato University) was inoculated into the large test tube containing Waksman broth (peptone 0.5%, meat extract 0.5%, NaCl 0.5% and glucose 2.0%) 10 ml, adding five glass beads (d=5 mm) therein, and shake cultured at 27° C. for 48 hours to obtain seed culture liquid.

This seed culture liquid was prepared in McFarland No. 0.5 (which had equal transparency with the mixture of 1% $NaCl_2$ solution 0.5 ml and 1% $H_2SO_4$ solution 9.95 ml at OD 630 nm) and diluted to 10-fold dilution (10-fold dilution culture bacterial solution: $10^7$ CFU/ml). Previously prepared series of drug dilution (3.9, 7.8, 15.6, 31.3, 62.5, 125, 250 and 500 μg/ml) each 5 μl/well was added to the 96 well microplate, to which Waksman broth 90 μl/well was previously added, and 10-fold dilution cultured bacterial liquid 5 μl/well was further added and mixed (final inoculated cell counts: $5 \times 10^4$ CFU/well) and incubated at 37° C. for 96 hours, and the concentration without observing bacterial growth was set to MIC.

MIC of K01-B0171-B substance was 3.13 μg/ml and that of K01-B0171-C substance was 6.25 μg/ml.

(3) Cytotoxicity Test

Jurkat cells cultured with RPMI medium were centrifuged at 1000 rpm for 10 minutes. Supernatant was removed by using aspirator. RPMI medium was newly added and adjusted cell counts $5 \times 10^5$ cells/ml to prepare cell suspension. Cell suspension 200 μl was added into the 96 well microplate added with samples and incubated at 37° C. for 20 hours. After cultivation, the well was centrifuged at 1000 rpm for 10 minutes and the supernatant was removed by using aspirator. Krishan's reagent (500 mg of trisodium citrate (Wako Pure Chemicals, Japan), 1.5 ml of IGEPAL CA-630 (Sigma Inc., the U.S.), 10 mg of ribonuclease A (Sigma Inc., the U.S.) and 25 mg of propydium iodide (Sigma Inc. the U.S.) were dissolved in sterilized water 500 ml) 200 μl was added to each well. The plate was sealed with aluminum foil to shade the light, then the plate was allowed to shake mildly at room temperature to stain DNA. After staining, measurement was performed by using FACS Calibur (Becton Dickinson Inc., the U.S.).

No cytotoxicity was indicated at the final concentration 50 μg/ml.

As explained in detail, K01-B0171 substance of the present invention has novel chemical skeleton and is expected to be useful novel antituberculous agent against tubercle bacillus.

BEST MODE FOR CARRYING OUT THE INVENTION

Figure 1:
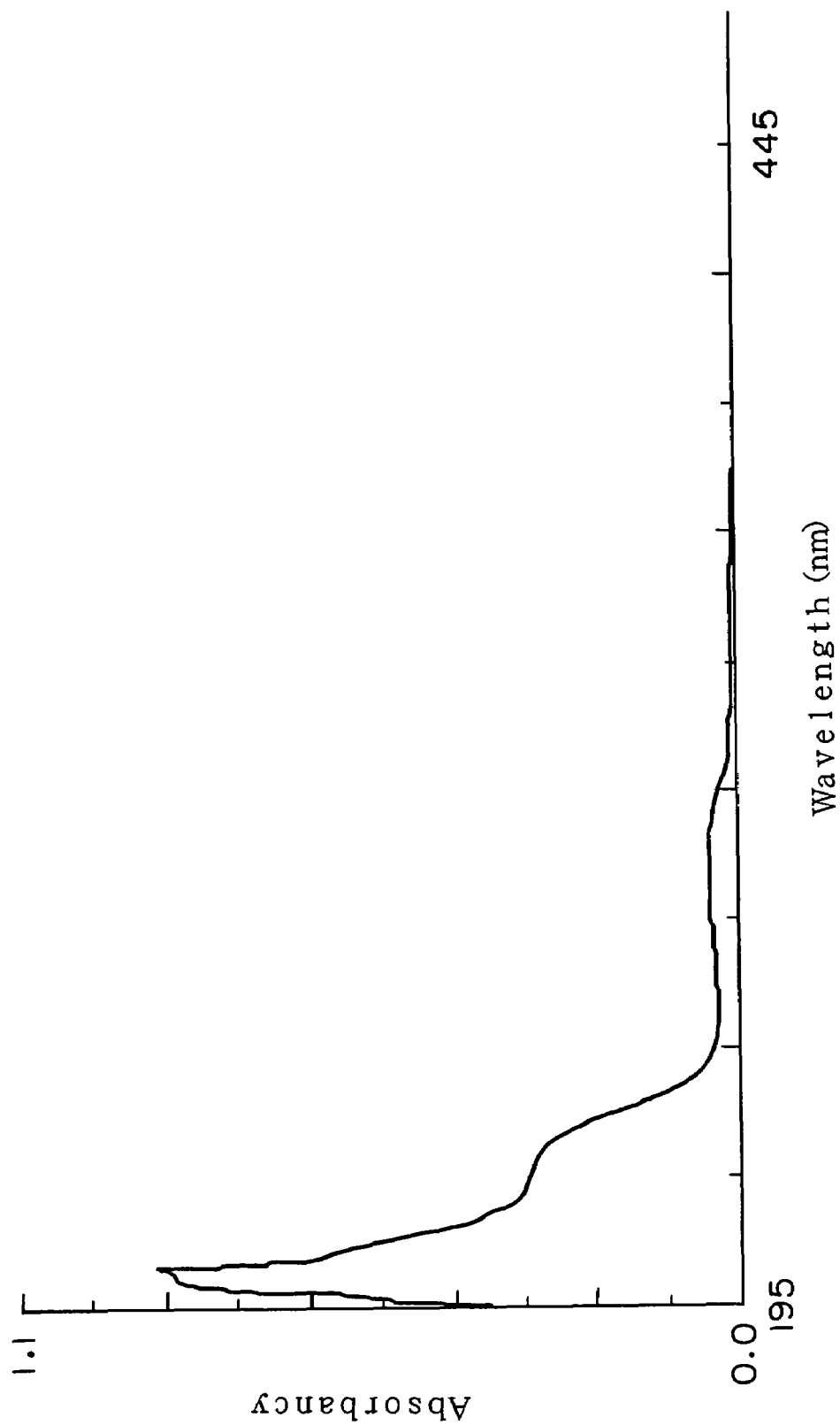
FIG. 1 shows UV spectrum of K01-B0171-B substance of the present invention (in 50% aqueous methanol).
Figure 2:
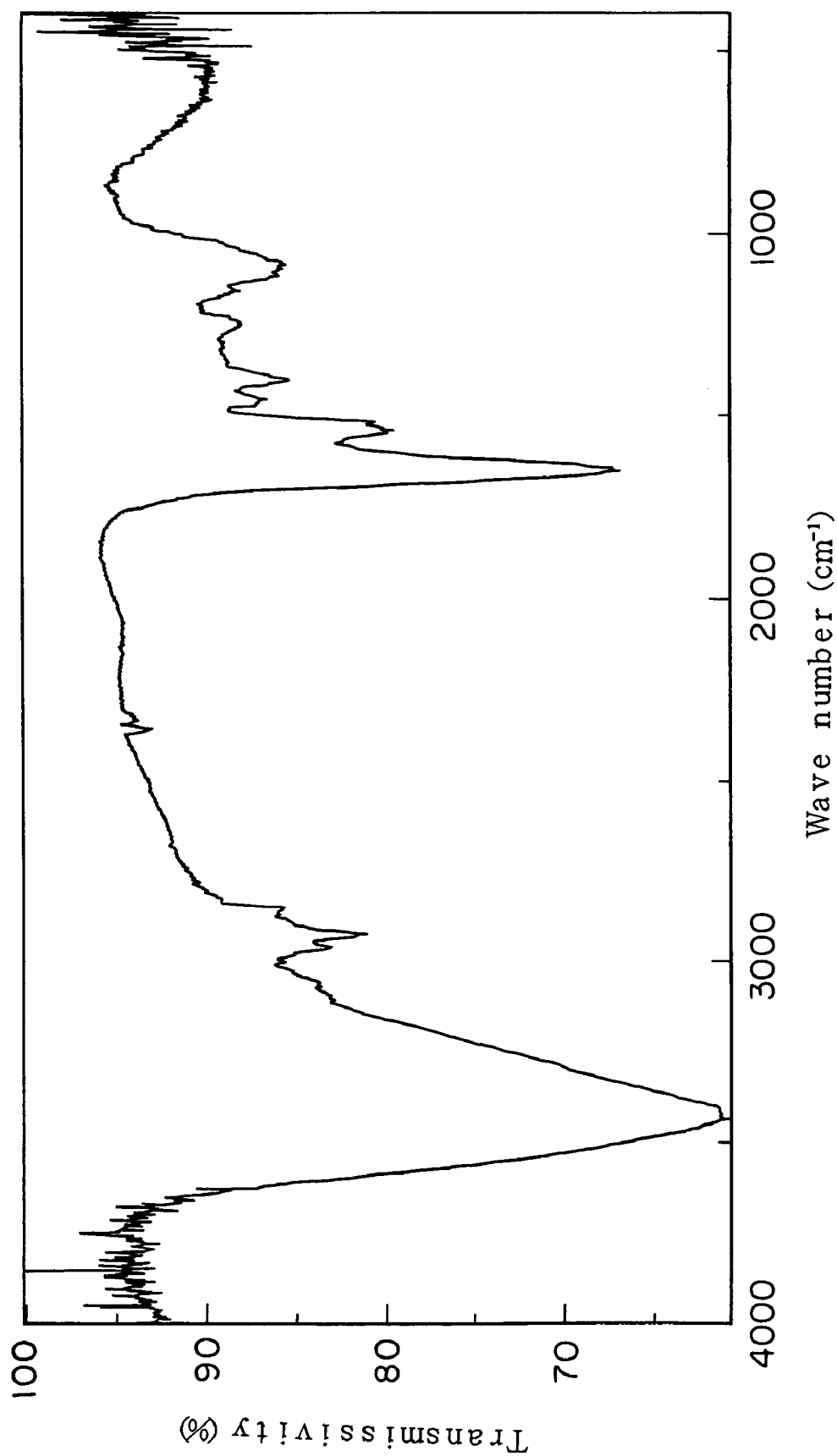
FIG. 2 shows IR spectrum of K01-B0171-B substance of the present invention (KBr tablet).
Figure 3:
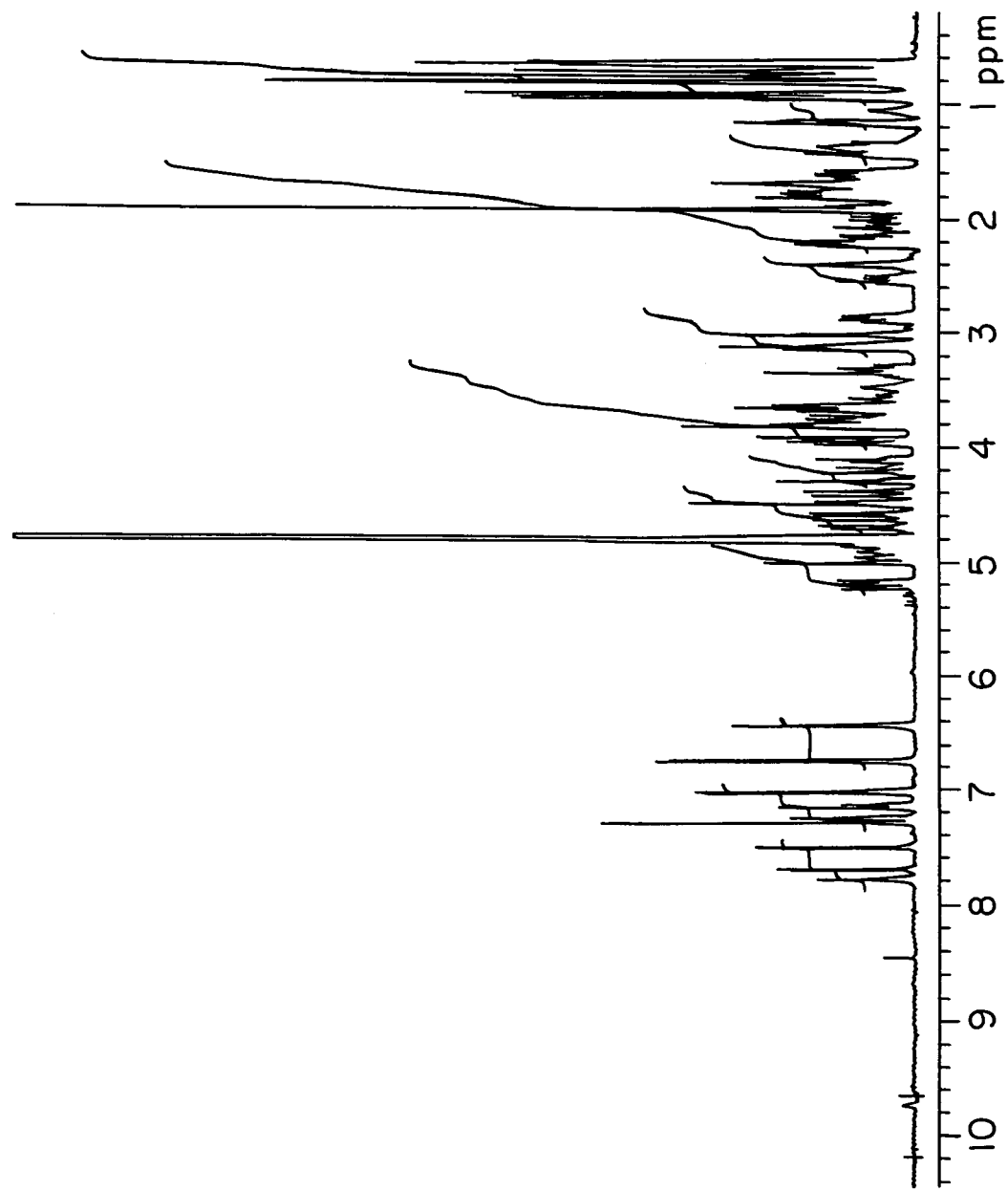
FIG. 3 shows proton NMR spectrum of K01-B0171-B substance of the present invention (in deuterium oxide).
Figure 4:
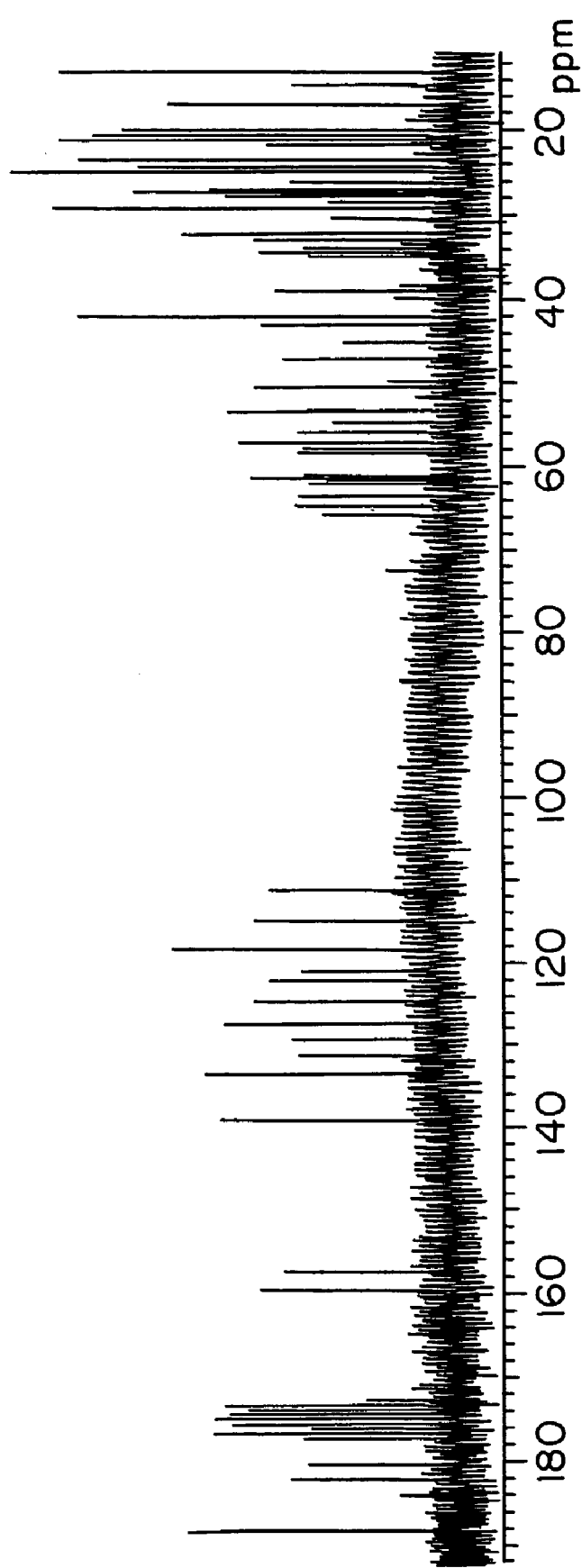
FIG. 4 shows carbon NMR spectrum of K01-B0171-B substance of the present invention (in deuterium oxide).
Figure 5:
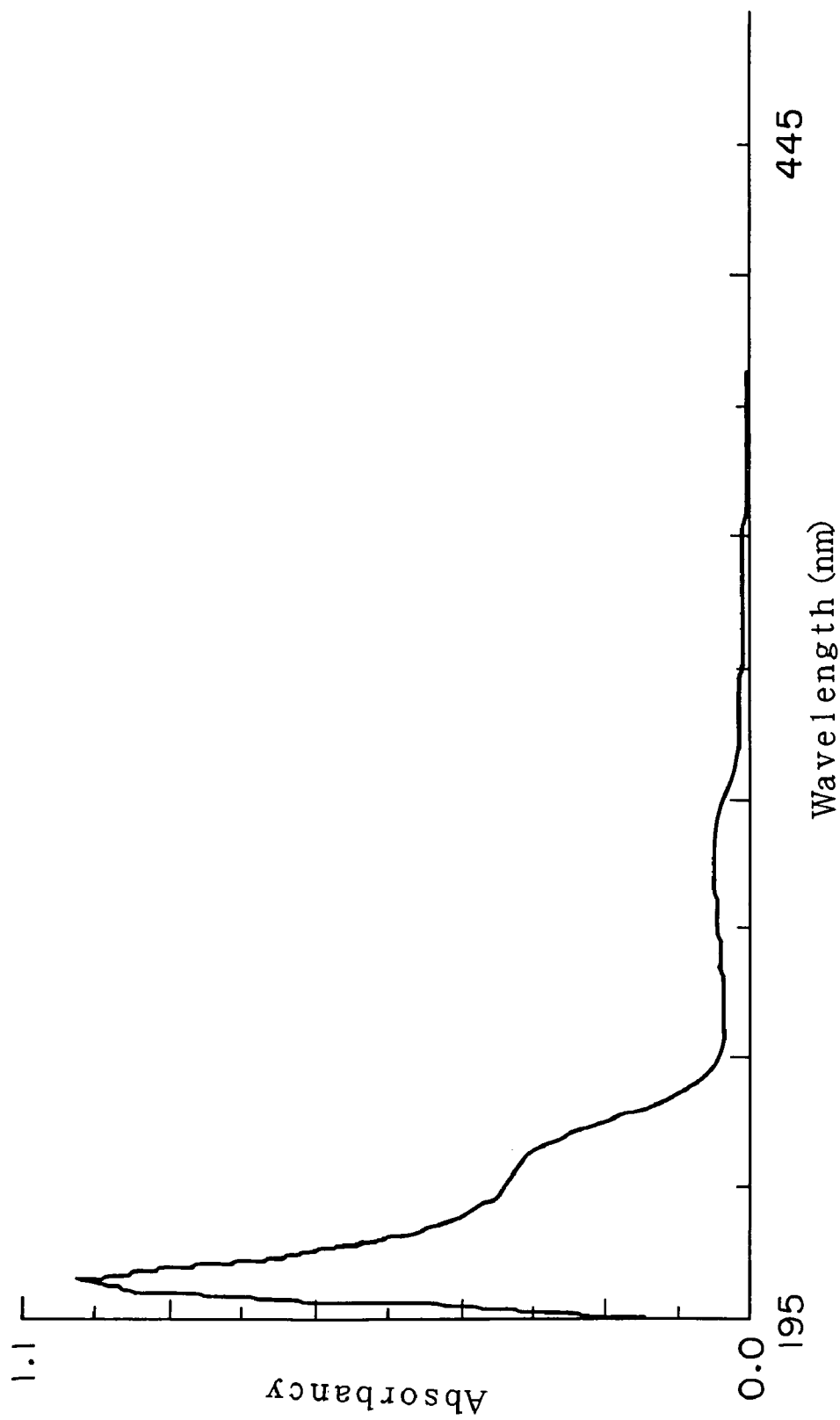
FIG. 5 shows UV spectrum of K01-B0171-C substance of the present invention (in 50% aqueous methanol).
Figure 6:
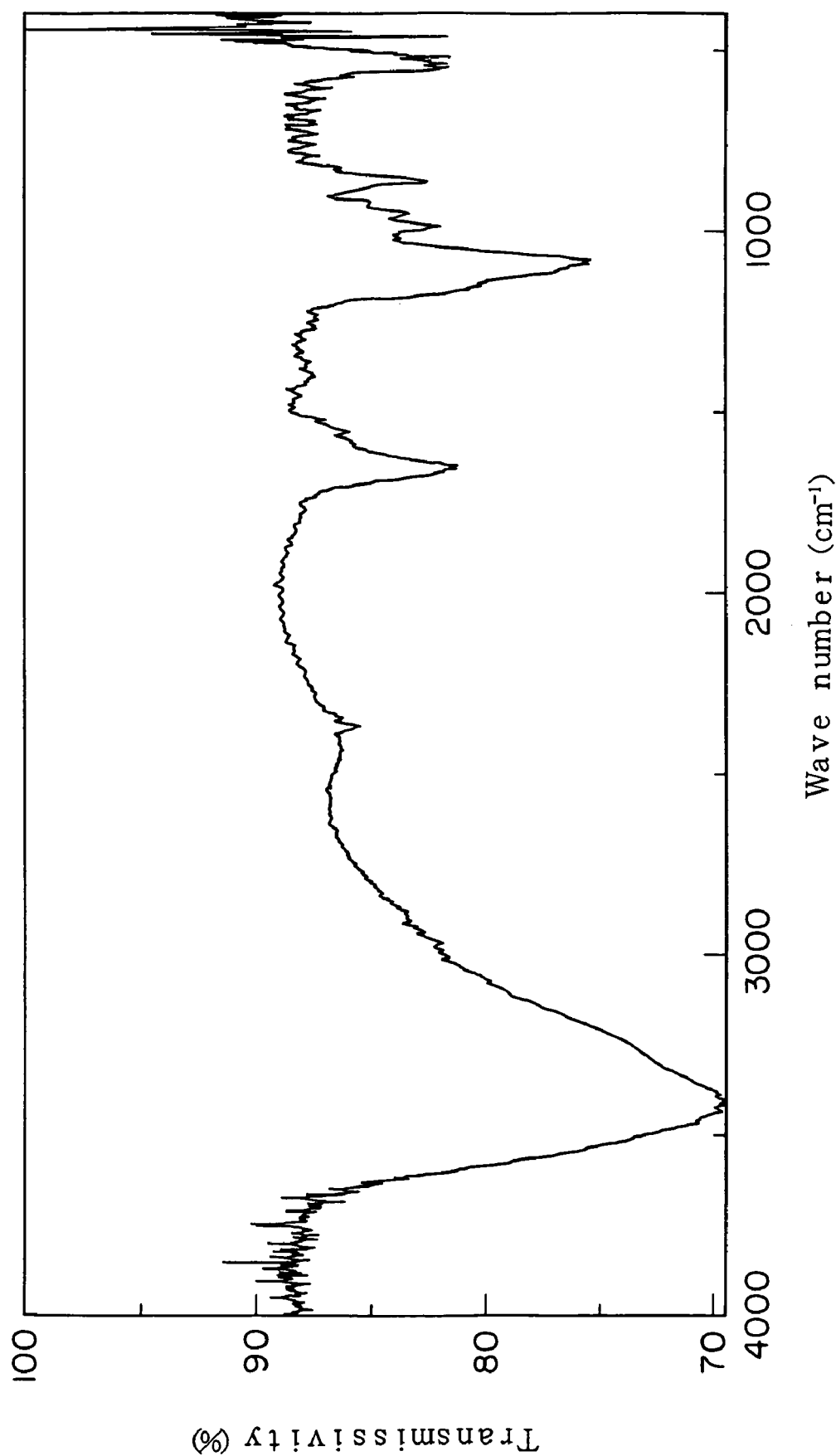
FIG. 6 shows IR spectrum of K01-B0171-C substance of the present invention (KBr tablet).
Figure 7:
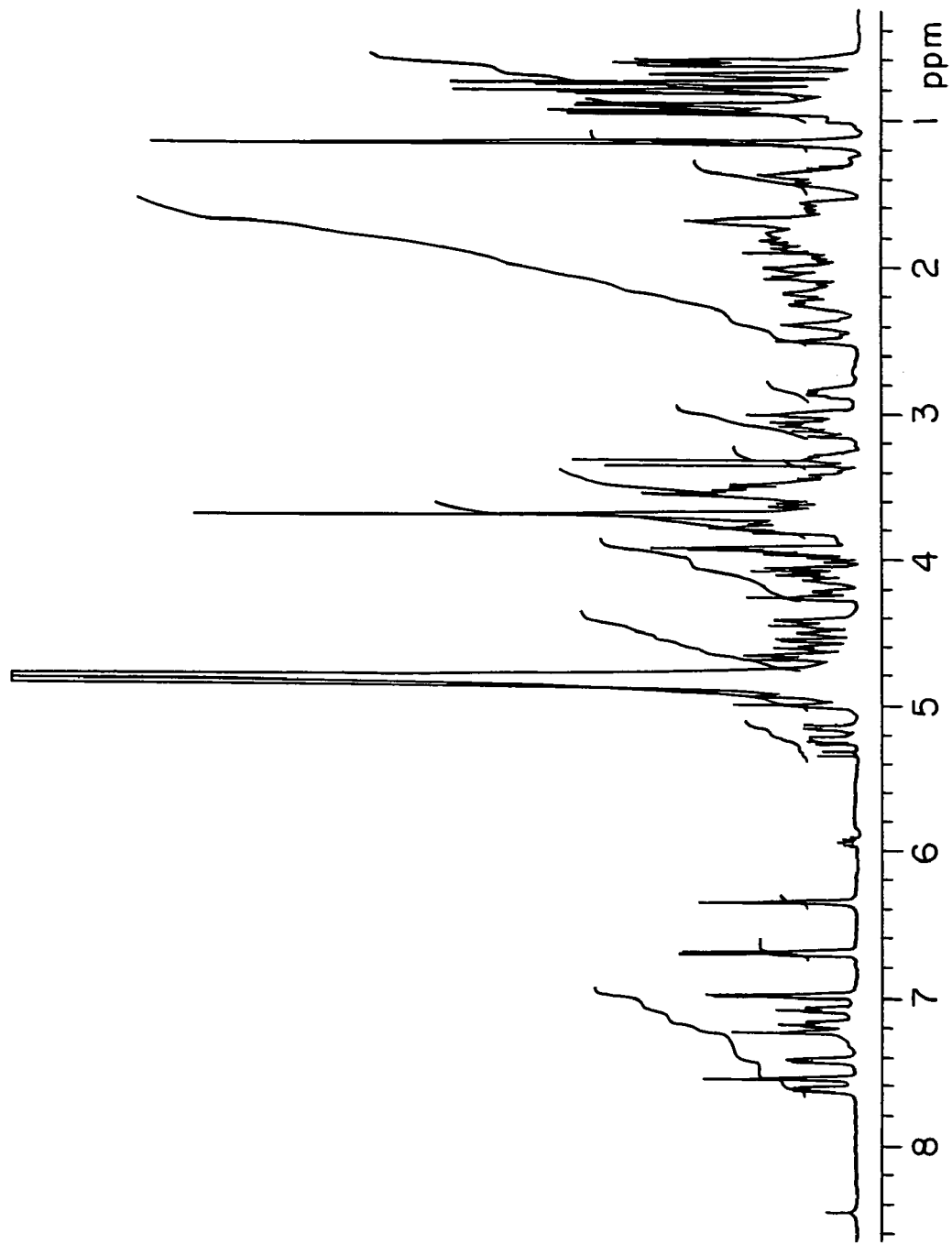
FIG. 7 shows proton NMR spectrum of K01-B0171-C substance of the present invention (in deuterium oxide—deuteriomethanol (3:2)).
Figure 8:
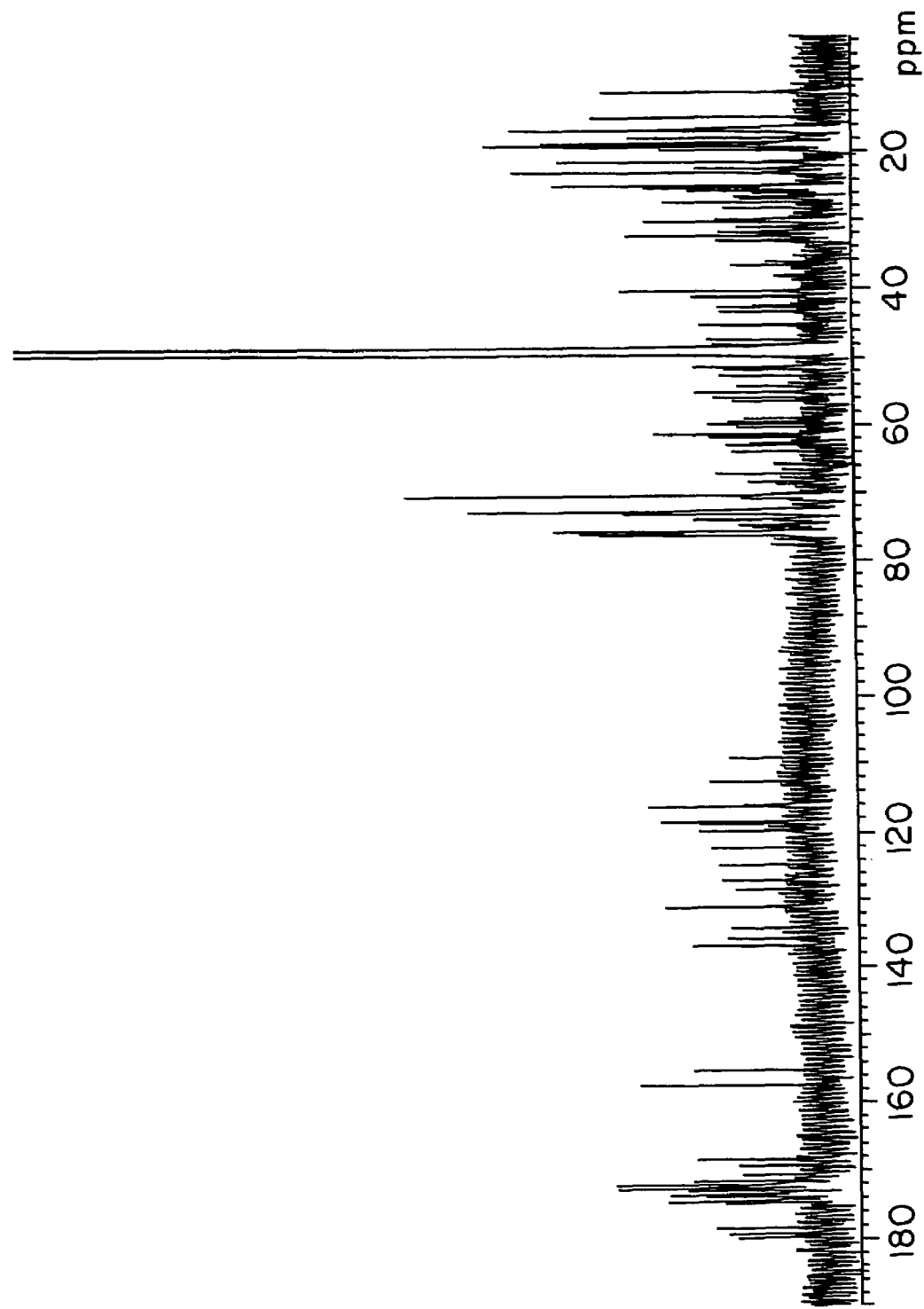
FIG. 8 shows carbon NMR spectrum of K01-B0171-C substance of the present invention (in light water—deuteriomethanol (3:2)).

The present invention is explained with example but the present invention is not limited within the example.

A loopful strain of *Rhodococcus* sp. K01-B0171 FERM BP-8267 cultured on agar slant medium (Seino medium) was inoculated into 500 ml Erlenmeyer flask containing seed culture medium (49 medium: mannitol 3.0%, glucose 1.0%, yeast extract 0.5%, MgSO$_4$.7H$_2$O 0.1%, ammonium succinate 0.5%, K$_2$HPO$_4$ 0.1% and trace metal solution (MgSO$_4$.7H$_2$O 0.0001%, FeSO$_4$.7H$_2$O 0.0001%, MgCl$_2$.4H$_2$O 0.0001%, ZnSO$_4$.7H$_2$O 0.0001%, CuSO$_4$.5H$_2$O 0.0001%, CoCl$_2$.6H$_2$O 0.0001%) 1 ml/l) 100 ml and cultured at 27° C. for 4 days in rotary shaker (210 rpm). The cultured medium was inoculated into 30 lit. jar-fermenter containing 20 lit. of production medium (49 medium: mannitol 3.0%, glucose 1.0%, yeast extract 0.5%, MgSO$_4$.7H$_2$O 0.1%, ammonium succinate 0.5%, K$_2$HPO$_4$ 0.1% and trace metal solution (MgSO$_4$.7H$_2$O 0.0001%, FeSO$_4$.7H$_2$O 0.0001%, MgCl$_2$.4H$_2$O 0.0001%, ZnSO$_4$.7H$_2$O 0.0001%, CuSO$_4$.5H$_2$O 0.0001%, CoCl$_2$.6H$_2$O 0.0001%) 1 ml/l) and cultured at 27° C. for 4 days.

The cultured liquid 50 ml was collected in time-dependent manner and pH, bacterial cell volume (the cultured medium was centrifuged at 10000 rpm for 15 minutes; amount of precipitation was converted to the amount corresponding to culture liquid 10 ml; and the cell volume was expressed by ml), anti-M. smegmatis activity (the supernatant 1 ml was treated with OASIS HLB (1 mg, Waters Inc., the U.S.), washed with water 1 ml and 20% acetonitrile 300 µl, eluted with 40% acetonitrile 300 µl, and assayed with using 50 µl/8 mm disk) were measured.

The cultured liquid (16 lit.), which was obtained from the above 4 days culture, was centrifuged by using Sharpless centrifuge (Kokusan Enshinki Co., Japan) to separate supernatant and mycelia. The supernatant was treated with Diaion HP-20 column (ϕ75×220 mm, Mitsubishi Chemicals Inc., Japan), washed with water and 20% acetone, each 3 lit., eluted the active principle with 80% acetone 3 lit., concentrated in vacuo and lyophilized. In the obtained crude substance 5 g, the crude substance 2 g was dissolved in small amount of methanol. The solution was applied with ODS column (ϕ35×270 mm, Senshu Sci. Co., Japan), washed with water and 20% acetonitrile, each 600 ml. The active principle was eluted with 40% acetonitrile 600 ml, concentrated in vacuo and dried in vacuo to obtain crude substance 154 mg. The active principle in the remaining crude substance 3 g was eluted by the same way, concentrated in vacuo and dried in vacuo to obtain crude substance 194 mg.

The thus obtained crude substance total 348 mg was dissolved in small amount of methanol, charged on a column of Sephadex LH-20 packed with methanol (ϕ2.5×110 cm, Pharmacia, Sweden), eluted with methanol at flow rate 1 ml/min., each 1 ml fraction, total 120 fractions, and the fractions containing active principle were concentrated and dried. Final purification was performed by using preparative HPLC (column: CAPCELL PAK, ϕ20×250 mm, Shiseido Inc., Japan). Isocratic mobile phase of 10 mM phosphate buffer (pH 7.5) –22% acetonitrile was used with flow rate 8 ml/min. and monitored by absorption at UV 210 nm. Peaks showing activity were observed at 44 min. and 56 min. to collect these peaks and concentrated.

100 times concentrated solution 2 ml was treated with OASIS HLB (3 mg, Waters Inc., the U.S.), washed with water 3 ml to desalt and eluted the active principle with 80% acetonitrile 2 ml. This operation was repeated to obtain the eluate. The eluate was concentrated and dried in vacuo, and lyophilized to isolate pale yellowish powder K01-B0171-B substance 38.3 mg (total yield 11.5%) and K01-B0171-C substance 11.2 mg (total yield 11.5%).

FIELD OF INDUSTRIAL APPLICATION

A microorganism represented by the strain K01-B0171 belonging to genus *Rhodococcus* having ability to produce K01-B0171-B substance and K01-B0171-C substance or composition thereof is cultured in a medium, and K01-B0171-B substance and K01-B0171-C substance or composition thereof are accumulated in the cultured liquid, and K01-B0171-B substance and K01-B0171-C substance or composition thereof are isolated from the cultured liquid. The thus obtained substance or composition has antituberculous activity and is expected as a medicament useful for prevention and treatment of tuberculosis.

What is claimed is:
1. An isolated K01-B0171-B compound represented by the following formula [I]
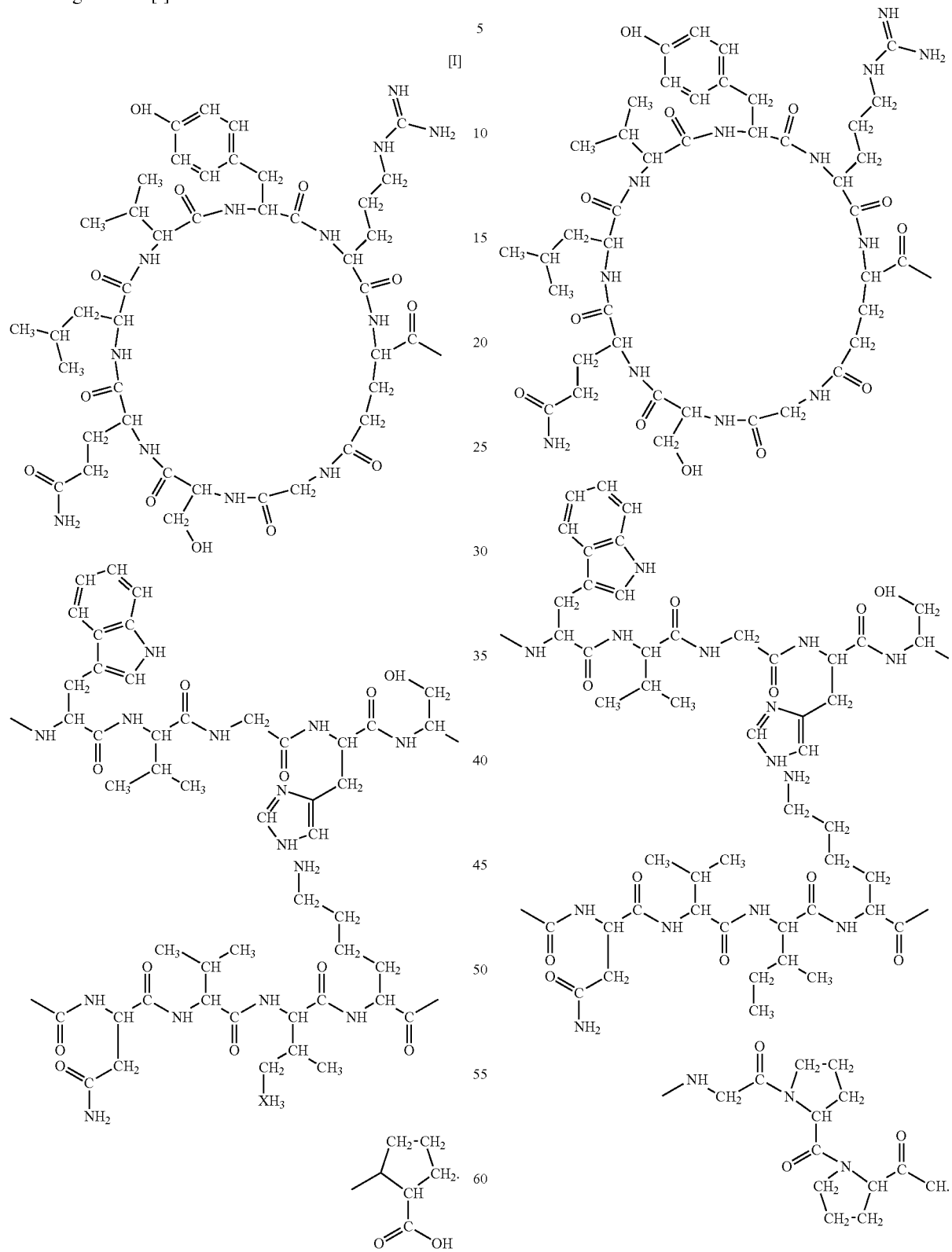
2. An isolated K01-B0171-C compound represented by the following formula [II]
3. A composition of a K01-B0171 compound comprising an isolated K01-B0171-B compound represented by the following formula [I]

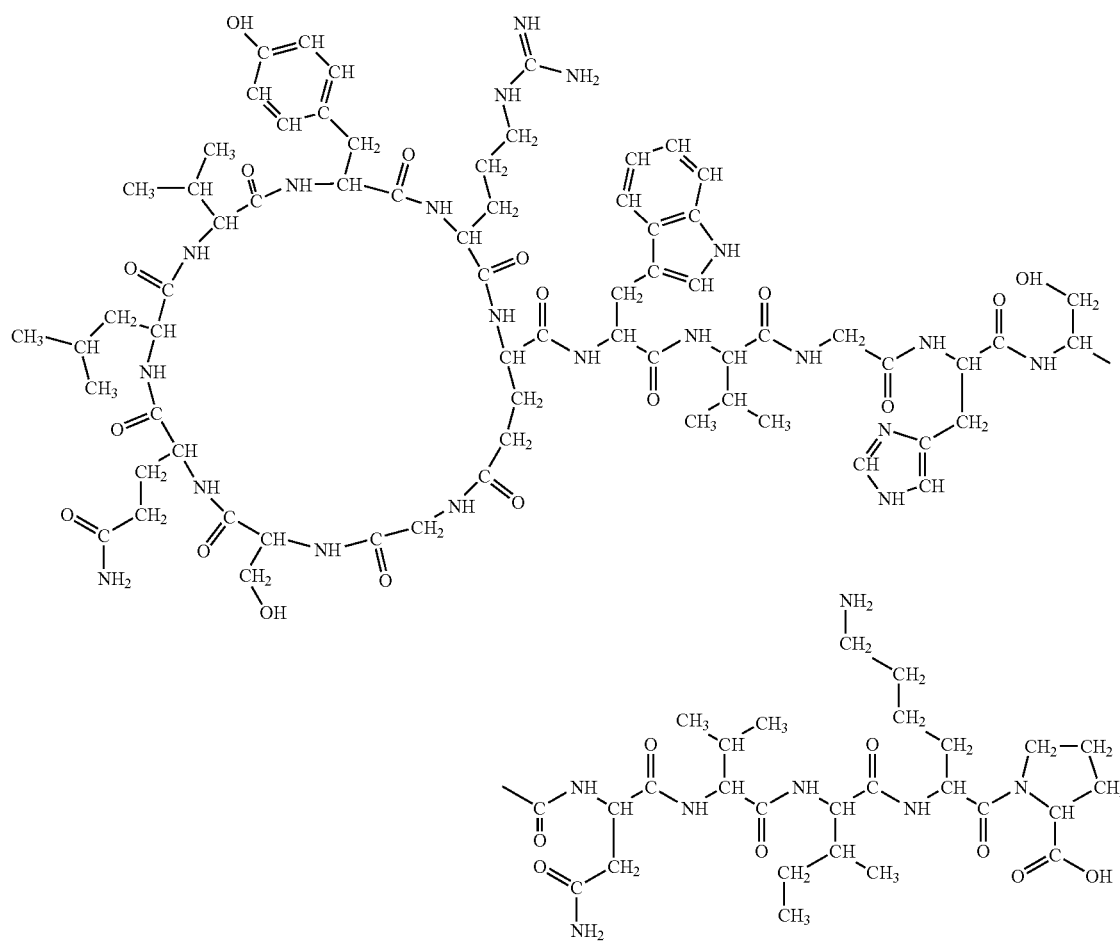
or an isolated K01-B0171-C compound represented by the following formula [II]
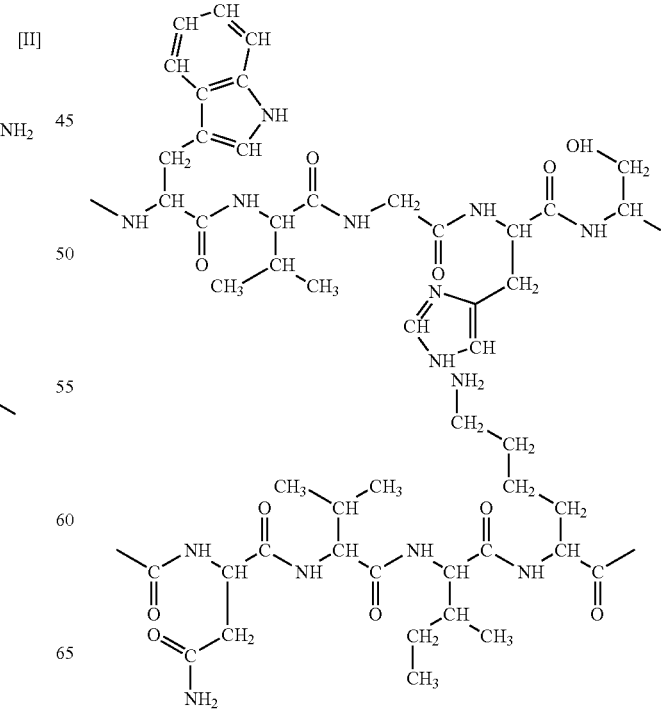

-continued

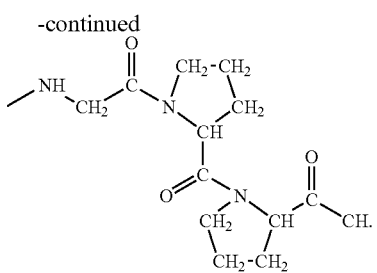

4. A process for production of an isolated K01-B0171-B compound, comprising:
culturing *Rhodococcus* sp. K01-B0171 FERN BP-8267 to produce a K01-B0171-B compound;
accumulating the K01-B0171-B compound in a culture fluid; and
isolating the K01-B0171-B compound from the culture fluid.

5. A process for production of an isolated K01-B0171-C compound, comprising:
culturing *Rhodococcus* sp. K01-B0171 FERN BP-8267 to produce a K01-B0171-C compound;
accumulating the K01-B0171-C compound in a culture fluid; and
isolating the K01-B0171-C compound from the culture fluid.

6. A process for production of a composition of an isolated K01-B0171 compound, comprising:
culturing *Rhodococcus* sp. K01-B0171 FERN BP-8267 to produce a K01-B0171-B compound and/or a K01-B0171-C compound;
accumulating the K01-B0171-B compound and/or the K01-B0171-C compound in a culture fluid; and
isolating the K01-B0171-B compound and/or the K01-B0171-C compound from the culture fluid.

7. A method for treating tuberculosis in a subject comprising administering to a subject in need thereof an effective amount of the compound according to claim 1.

8. A method for treating tuberculosis in a subject comprising administering to a subject in need thereof an effective amount of the compound according to claim 2.

9. A method for treating tuberculosis in a subject comprising administering to a subject in need thereof an effective amount of the composition according to claim 3.

\* \* \* \* \*

SEQUENCE LISTING

```
<160> NUMBER OF SEQ ID NOS: 2

<210> SEQ ID NO 1
<211> LENGTH: 18
<212> TYPE: PRT
<213> ORGANISM: Rhodococcus sp.

<400> SEQUENCE: 1

Gly Ser Gln Leu Val Tyr Arg Glu Trp Val Gly His Ser Asn Val Ile
 1               5                  10                  15

Lys Pro

<210> SEQ ID NO 2
<211> LENGTH: 20
<212> TYPE: PRT
<213> ORGANISM: Rhodococcus sp.

<400> SEQUENCE: 2

Gly Ser Gln Leu Val Tyr Arg Glu Trp Val Gly His Ser Asn Val Ile
 1               5                  10                  15

Lys Gly Pro Pro
            20
```